United States Patent [19]

Lin et al.

[11] Patent Number: 4,525,481

[45] Date of Patent: Jun. 25, 1985

[54] ACETALDEHYDE PRODUCTION FROM SYNTHESIS GAS

[75] Inventors: Jiang-Jen Lin, Round Rock; John F. Knifton, Austin, both of Tex.

[73] Assignee: Texaco Inc., White Plains, N.Y.

[21] Appl. No.: 584,076

[22] Filed: Feb. 27, 1984

[51] Int. Cl.$^3$ .............................................. C07C 27/06
[52] U.S. Cl. .................... 518/700; 518/715; 518/716; 502/150
[58] Field of Search ................ 518/700, 715, 716

[56] References Cited

U.S. PATENT DOCUMENTS 4,332,915  6/1982  Knifton et al. .................. 518/700
4,366,259  12/1982  Knifton et al. .................. 518/715

*Primary Examiner*—Howard T. Mars
*Attorney, Agent, or Firm*—Jack H. Park; Kenneth R. Priem; David L. Mossman

[57] ABSTRACT

Acetaldehyde is prepared by contacting hydrogen and carbon monoxide with a catalyst system comprising an iodide-free ruthenium powder, an iodide-free quaternary phosphonium or ammonium base or salt and a halide-free cobalt-containing compound, such as cobalt-(III) acetylacetonate or dicobalt octacarbonyl. Conducting the reaction in a substantially inert solvent such as p-dioxane is preferred.

12 Claims, No Drawings

ACETALDEHYDE PRODUCTION FROM SYNTHESIS GAS

BACKGROUND OF THE INVENTION

1. Field of the Invention

This invention relates to an improved process for preparing acetaldehyde selectively from hydrogen and carbon monoxide directly.

2. Description of Other Related Processes in the Field

Acetaldehyde is a well known chemical, useful in the production of materials such as acetic acid, acetic anhydride, n-butanol, 2-ethylhexanol, peracetic acid, pentaerythritol, pyridines, chloral, 1,3-butylene glycol and trimethylolpropane. Acetaldehyde has been produced conventionally by methods such as the hydration of acetylene or the oxidation of ethylene, but such methods have their limitations, particularly as to cost and it would be desirable to find a more economic method for the preparation of this compound.

A great number of processes have been described in the art for reacting methanol and other C-1 derived chemicals such as formaldehyde and methyl acetate with carbon monoxide and hydrogen in the presence of catalyst systems to produce a wide variety of compounds. A general disadvantage of the art described processes is that they all produce a wide variety of by-products such as higher molecular weight alcohols, aldehydes, hydrocarbons, carboxylic acids, esters, etc. in addition to the desired one.

U.S. Pat. No. 4,151,208 teaches that acetaldehyde may be selectively produced by contacting methanol, hydrogen and carbon monoxide with cobalt(II) mesotetraaromatic porphine and an iodine promoter.

Other examples for acetaldehyde synthesis from methanol and $CO/H_2$ are seen in U.S. Pat. Nos. 4,239,704; 4,239,705; 4,225,517; 4,201,868; 4,337,365; 4,306,091 and 4,348,541, *J. Molecular Catalysis*, Vol. 17 (1982), 339–347, *Organometallics*, Vol. 2, No. 12 (1983), 1881, and European Pat. Nos. 11042, 37588 and 22735. Most of these catalysts involved and use of homogeneous cobalt and/or ruthenium compounds with an iodine promoter.

A palladium catalyst with iodide promoter was disclosed by Halcon in Ger. Offen. No. 2,952,517 and U.S. Pat. No. 4,302,611 for acetaldehyde synthesis from the reaction of methyl acetate and $CO/H_2$.

Furthermore, National Distillers and Chemical Corp. disclosed in U.S. Pat. Nos. 4,291,179 and 4,267,384 the conversion of formaldehyde into acetaldehyde by the use of rhodium and ruthenium catalysts.

Processes for making a distribution of two-carbon atom oxygenated hydrocarbons such as acetic acid, ethanol and acetaldehyde are well known. For example, U.S. Pat. No. 4,014,913 teaches a method for making these three latter compounds by continuously reacting synthesis gas (hydrogen and carbon monoxide) with a rhodium-manganese catalyst system. A similar product distribution results when synthesis gas is reacted over a solid catalyst comprising rhodium in combination with molybdenum and/or tungsten according to U.S. Pat. No. 4,096,164. A similar technique using a rhodium and thorium and/or uranium system is noted in U.S. Pat. No. 4,162,262.

A homogeneous ruthenium catalyst has been disclosed in Fischer-Tropsch type reaction for producing oxygenates directly from synthesis gas. For example, in U.S. Pat. Nos. 4,301,253 (Nov. 17, 1981) and 4,333,852 (June 8, 1982), alkanols are selectively produced as the major product directly from synthesis gas under mild conditions, using a homogeneous ruthenium catalyst, a halogen or halide promoter, especially elemental iodine, and a phosphine oxide compound as solvent. There are related disclosures in *J. Amer. Chem. Soc.* (1981), 103, pp. 6508–6510; *J. Amer. Chem. Soc.* (1980), 102, pp. 6855–6857; *J.C.S. Chem. Comm.* (1980), p. 1098 and *J.C.S. Chem. Comm.* (1980), p. 1101.

The use of phosphonium salt or base in combination with a homogeneous ruthenium catalyst for oxygenates synthesis from synthesis gas directly has been disclosed in U.S. Pat. Nos. 4,366,259 (Dec. 28, 1982); 4,362,821 (Dec. 7, 1982) and 4,332,915 (June 1, 1982) to Texaco Inc. In these cases, a homogeneous ruthenium compound is used and alkanols/esters and carboxylic acid are the major products.

The selective synthesis of acetaldehyde by carbon monoxide hydrogenation is relatively difficult to achieve due to the instability of acetaldehyde under the usual reaction conditions. For example, in *Chemistry Letters*, pp. 131–134, 1982, there is disclosed that a rhodium catalyst supported by silica gel and pretreated at certain conditions produced ethanol and acetaldehyde with hydrocarbon by-products under the synthesis gas conditions. In another example (European patent application EP No. 45,620), synthesis gas was contacted with Rh-Ag mixtures at 150°–450°/1–700 bar to yield acetaldehyde, ethanol, methanol, acetic acid and hydrocarbons. A mixture of ruthenium carbonyl and lithium chloride at 200° C. and synthesis gas conditions produced methanol, acetaldehyde and ethanol which is disclosed by Fr. Demande FR 2,480,743 (National Distillers and Chemical Corp.). In *J. of Catalysis*, (1978), Vol. 54, p. 120, Bhasin, et al. discuss the conversion of synthesis gas over supported rhodium and rhodium-iron catalysts.

Catalysts similar, but not identical, to the ones used herein are employed in processes to make ethanol from the homologation of methanol with synthesis gas described in U.S. Pat. Nos. 4,371,724; 4,374,285 and 4,424,384. U.S. Pat. No. 4,433,178 teaches a method for making acetaldehyde in good yield from methanol and synthesis gas via contact with a ruthenium-cobalt-quaternary onium salt or base. A process similar to that of U.S. Pat. No. 4,433,178 is disclosed in U.S. Pat. No. 4,433,176 except that rhodium is also included in the catalyst system. Finally U.S. patent application Ser. No. 344,260 filed on Feb. 1, 1982, also describes a process similar to that of U.S. Pat. No. 4,433,178, except that an amine is also present in the catalyst system.

All of the processes described above suffer from one or more disadvantages. In many cases, the conversion is low, decomposition of the catalyst to insoluble and inactive species is observed and a wide variety of products in addition to the desired acetaldehyde are formed with consequent separation and disposal problems. There is a major disadvantage when iodine is used as part of the various catalyst systems. Iodine is very corrosive and, when used in industrial processes, is very difficult to dispose of. The catalyst which is the object of this invention comprises a ruthenium compound, a quaternary phosphonium or ammonium base or salt and a cobalt compound in a commercially attractive iodide-free system.

SUMMARY OF THE INVENTION

The invention concerns a process for preparing acetaldehyde. Carbon monoxide and hydrogen are contacted with an iodide-free catalyst system comprising elemental ruthenium, an iodide-free quaternary phosphonium or ammonium base or salt and a halide-free cobalt containing compound. The pressure is about 500 psig or greater and the temperature is about 150° C. or greater.

Recovery of acetaldehyde from the reaction product can be carried out in any conventional or convenient manner such as by distillation, extraction, etc.

DETAILED DESCRIPTION OF THE INVENTION

The catalyst system suitable for the practice of this invention comprises an iodide-free ruthenium-containing compound, an iodide-free quaternary phosphonium base or salt and a halide-free cobalt compound as exemplified by cobalt(III) acetylacetonate or dicobalt octacarbonyl.

A higher degree of conversion of reactants to the desired acetaldehyde is achieved with the above-described catalyst combination. Also, the stability of this catalyst system is such that it can be conveniently recovered from the reaction mixture and recycled to the process.

Generally, with regard to the metallic components of the catalyst system it will contain from about 15 to about 80 mole percent of the ruthenium compound with the balance being halide-free cobalt compound based on the total number of moles of the ruthenium compound and the total number of moles of the cobalt compound in the system. Preferably, the catalyst system will contain about equimolar amounts of the ruthenium and cobalt compounds.

The iodide-free ruthenium compounds useful in this invention include any of the ruthenium oxides, such as, for example, ruthenium(IV) dioxide hydrate, anhydrous ruthenium(IV) dioxide and ruthenium(VIII) tetraoxide.

Alternatively, ruthenium may be added as the salt of certain mineral acids, as in the case of ruthenium(III) chloride hydrate, ruthenium(III) bromide, anhydrous ruthenium(III) chloride and ruthenium nitrate, or as the salt of a suitable organic carboxylic acid, for example ruthenium(III) acetate, ruthenium(III) propionate, ruthenium butyrate, ruthenium(III) trifluoroacetate, ruthenium octanoate, ruthenium(III) trifluoroacetate, ruthenium octanoate, ruthenium naphthenate, ruthenium valerate and ruthenium(III) acetylacetonate. The ruthenium may also be added to the reaction zone as a carbonyl or hydrocarbonyl derivative. Other examples include triruthenium dodecacarbonyl, hydrocarbonyls, such as $H_2Ru_4(CO)_{13}$ and $H_4Ru_4(CO)_{12}$ and substituted carbonyl species such as the tricarbonyl ruthenium(II) chloride dimer $[Ru(CO)_3Cl_2]_2$.

Although all of these ruthenium compounds would be useful in the production of acetaldehyde, the best results in accordance with the present invention are obtained only when elemental ruthenium is used as a ruthenium source, such as in the form of ruthenium powder of any mesh size. However, a second preferred embodiment is the use of ruthenium powder in combination with one or more of the iodide-free ruthenium compounds described supra.

A wide variety of halide-free cobalt compounds are useful in the catalyst system of this invention. These halide-free containing compounds may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise cobalt in complex combination with carbon monoxide and hydrogen.

The halide-free cobalt-containing catalyst precursors may take many different forms. For instance, the cobalt may be added to the reaction mixture in an oxide form, as in the case of, for example, cobalt(II) oxide, (CoO) or cobalt(II,III) oxide ($Co_3O_4$). Alternatively, it may be added as the salt of a halide-free mineral acid, as in the case of cobalt(II) nitrate hydrate [$Co(NO_3)_2 \cdot 6H_2O$] cobalt(II) phosphate, cobalt(II) sulfate, etc., or as the salt of a suitable organic carboxylic acid; for example, cobalt(II) formate, cobalt(II) acetate, cobalt (II) propionate, cobalt naphthenate, cobalt acetylacetonate, etc. The cobalt may also be added to the reaction zone as a halide-free carbonyl or hydrocarbonyl derivative. Here, suitable examples include dicobalt octacarbonyl, [$Co_2(CO)_8$], cobalt hydrocarbonyl [$HCo(CO)_4$] and substituted carbonyl species such as the triphenylphosphine cobalt tricarbonyl dimer, etc.

Preferred cobalt-containing compounds include oxides of cobalt, cobalt salts of a halide-free mineral acid, cobalt salts or organic carboxylic acids and cobalt carbonyl or hydrocarbonyl derivatives. Among these, particularly preferred are cobalt acetylacetonate, cobalt(II) acetate, cobalt(II) propionate and dicobalt octacarbonyl.

Quaternary phosphonium and ammonium salts suitable for use in this process have the formula:

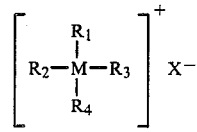

where M is phosphorous or nitrogen, $R_1$, $R_2$, $R_3$ and $R_4$ are organic radicals, particularly alkyl, aryl or alkaryl radicals bonded to the phosphorous or nitrogen atom, and X is an anionic species other than iodide. The organic radicals useful in this instance include these alkyl radicals having 1 to 20 carbon atoms in a branched or linear alkyl chain. They include, for example, the methyl, ethyl, n-butyl, iso-butyl, octyl, 2-ethylhexyl and dodecyl radicals. Tetraoctylphosphonium bromide and tetrabutylphosphonium bromide are typical examples presently in commercial production. The corresponding quaternary phosphonium and ammonium acetate, hydroxides, chloride, nitrates, chromates and tetrafluoroborates are also satisfactory in this instance. Also useful are the corresponding quaternary ammonium bases and salts of the above series of compounds.

Equally useful are the iodide-free phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$–$C_{10}$ alkyl substituents, bonded to the phosphorus or nitrogen atom through the aryl function.

Illustrative examples of suitable iodide-free quaternary phosphonium and ammonium bases and salts include tetrabutylphosphonium bromide, tetraoctylphosphonium bromide, heptyltriphenylphosphonium bromide, tetrabutylphosphonium chloride, tetrabutylphosphonium nitrate, tetrabutylphosphonium hydroxide, (n-butyl)triphenylphosphonium bromide, (n-dodecyl)triphenylphosphonium bromide, tetrabutylphosphonium tetrafluoroborate, tetrabutylphosphonium acetate, tetrabutylammonium bromide, tetramethylammonium bromide and trimethyldodecylammonium bromide.

The preferred iodide-free quaternary salts are generally the tetraalkylphosphonium or alkyl-triaryl phosphonium salts containing alkyl groups having 3 to 8 carbon atoms, such as butyl, hexyl and octyl and where the aryl group is phenyl. Iodide-free tetrabutylphosphonium salts, such as tetrabutylphosphonium bromide, constitute a preferred group of tetraalkylphosphonium salts for the practice of this invention.

Preferred iodide-free tetrabutylphosphonium salts or bases include the bromide, chloride, acetate salts and hydroxide base. Preferred iodide-free alkyl-triaryl phosphonium salts include, for example, heptyltriphenylphosphonium bromide, butyltriphenylphosphonium bromide, and methyltriphenylphosphonium bromide as well as the corresponding chlorides.

Generally, in the catalyst system the molar ratio of the ruthenium compound to the quaternary phosphonium or ammonium salt or base will range from about 1:0.01 to about 1:100 or more, and preferably will be from about 1:0.5 to about 1:20.

The quantity of ruthenium compound employed in the instant invention is not critical and may vary over a wide range. In general, the novel process is desirably conducted in the presence of a catalytically effective quantity of the active ruthenium species and of the cobalt compound which gives the desired product in reasonable yield. The reaction proceeds when employing as little as about $1 \times 10^{-6}$ wt.%, and even lesser amounts of ruthenium, together with about $1 \times 10^{-6}$ wt.% or less of cobalt, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 5 wt.% in conjunction with a cobalt concentration of from about $1 \times 10^{-5}$ to about 5 wt.%, based on the total weight of reaction mixture is generally desirable in the practice of this invention.

A wide variety of substantially inert solvents are useful in the process of this invention including hydrocarbon and oxygenated hydrocarbon solvents. Suitable oxygenated hydrocarbon solvents are compounds composed only of carbon, hydrogen and oxygen and those in which the only oxygen atoms present are in ether groups, ester groups, ketone carbonyl groups or hydroxyl groups of alcohols. Generally, the oxygenated hydrocarbon will contain 3 to 12 carbon atoms, and preferably a maximum of 3 oxygen atoms. The solvent must be substantially inert under reaction conditions, it must be relatively non-polar and it must be one which has a normal boiling point of at least 65° C. at atmospheric pressure. Preferably, the solvent will have a boiling point greater than that of acetaldehyde and other oxygen-containing reaction products so that recovery of the solvent by distillation is facilitated.

Preferred ester type solvents are the aliphatic and acyclic carboxylic acid monoesters as exemplified by butyl acetate, methyl benzoate, isopropyl iso-butyrate and propyl propionate as well as dimethyl adipate. Useful alcohol-type solvents include monohydric alcohols such as cyclohexanol, 1-hexanol, 2-hexanol, pentanol, 2-octanol, etc. Suitable ketone-type solvents include, for example, cyclic ketones such as cyclohexanone, 2-methylcyclohexanone, as well as acylic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers such as 1,4-dioxane or p-dioxane, etc. Hydrocarbon non-polar solvents, such as hexane, heptane, decane, dodecane, tetradecane, etc. are also suitable solvents for use in this invention.

In the practice of this invention, it is also possible to add a small amount of water to the solvent and still obtain satisfactory results.

If an inert solvent such as p-dioxane is employed, it is preferred that a co-catalyst be employed to help enhance the selectivity to the desired acetaldehyde rather than another of the many possible by-products. The preferred co-catalysts are one or more rhodium-containing compounds, such as rhodium chloride.

The temperature range which can usefully be employed in these syntheses is a variable dependent upon other experimental factors, including the pressure, and the concentration and choice of a particular species of ruthenium catalyst, cobalt catalyst and quaternary compound utilized among other things. The range of operability is from about 150° C. to about 350° C. when superatmospheric pressures of syngas (synthesis gas) are employed. A narrow range of about 180°–250° C. represents the preferred temperature range.

Superatmospheric pressures of 500 psig or greater lead to substantial yields of acetaldehyde by the process of this invention. A preferred operating range is from about 2,000 psig to about 100,000 psig, although pressures above 10,000 psig also provide useful yields of acetaldehyde.

The relative amounts of carbon monoxide and hydrogen which may be initially present in the syngas mixture can be varied widely. In general, the mole ratio of CO to $H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methyl ether and diethyl ether, alkanols such as methanol and acid esters such as methyl acetate.

Alcohols and carboxylic acid esters may also be formed while carrying out the process of this invention. Most often these derivatives are methanol, ethanol, n-propanol, methyl formate, methyl acetate, ethyl acetate, ethyl ether, etc. The major by-products of the process such as the higher molecular weight alcohols and carboxylic acid esters, are, of course, also useful compounds and major articles of commerce. The higher alcohols, the carboxylic acid esters and ethers can easily be separated from one another by conventional means; e.g., fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the acetaldehyde product, and after recovery of the aldehyde and other products, a fraction rich in ruthenium and cobalt catalyst components may then be recycled to the reaction zone, if desired, and additional products generated.

The products have been identified in this work by one or more of the following analytical procedures; viz, gas-liquid phase chromatograph (GLC), infrared (IR), mass spectrometry, nuclear magnetic resonance (NMR) and elemental analyses, or a combination of these techniques. Analyses have, for the most part, been by parts in weight. All temperatures are in degrees centigrade and all pressure in pounds per square inch gauge (psig).

The mole percent selectivities to acetaldehyde, as well as other major products of these syntheses, particularly methanol, ethyl acetate and acetic acid, have been estimated in this work using the formula:

$$\frac{W_x}{\Sigma W_x} \text{ (multiplied by 100\%)}$$

where $x$ = the product of interest; e.g., acetaldehyde, ethanol, methanol, acetic acid, methyl acetate or ethyl acetate.

$W_x$ = the wt.% of the product x in the crude liquid product, as determined by GLC.

Various embodiments of the process of this invention are illustrated in the following examples which are not to be considered limitative.

EXAMPLES 1-11

These examples illustrate the preparation of acetaldehyde ($CH_3CHO$) directly from synthesis gas. Each example uses as catalyst precursors ruthenium powder, dicobalt octacarbonyl and tetrabutylphosphonium bromide. The solvent is p-dioxane. In Examples 5-10, a second ruthenium source; namely, ruthenium(IV) oxide, has been included also. Rhodium(III) chloride is used in Example 11 as an additional co-catalyst.

EXAMPLE 1

A 183 ml glass-lined reactor was charged with ruthenium powder (0.050 g, 0.5 mmole) tetra-n-butylphosphonium bromide (3.40 g, 10 mmoles) dicobalt octacarbonyl (0.34 g, 1 mmole) and p-dioxane (15 ml). The reactor was flushed with syngas, sealed and pressured to 1,000 psi with $CO/H_2 = 1:2$ molar ratio syngas, then heated to 200° C. with agitation. The pressure was brought up to 6,300 psi and these conditions maintained for 17 hours. Then the reactor was allowed to cool and the off-gas sample was taken via a gas bomb. The liquid sample was analyzed by gas-liquid chromatography and showed:

Acetaldehyde, %: 3.6
Ethyl acetate, %: 1.7
p-Dioxane, %: 94

The product selectivities are calculated to be 60% for acetaldehyde and 28% for ethyl acetate.

The off-gas showed the composition of:
CO, %: 52
$H_2$, %: 25
$CH_4$, %: 0
$CO_2$, %: 1.2

Other examples are summarized in Table I showing the relative product selectivities.

TABLE I

Acetaldehyde Production from $CO/H_2$ Directly

| Example | Catalysts (mmole used) | p-dioxane Solvent, ml | Reaction Conditions | Product Selectivity, wt. % | | | | | | Productivity (g/mole Ru/hr) |
|---|---|---|---|---|---|---|---|---|---|---|
| | | | | MeOH | $CH_3CHO$ | EtOH | MeOAc | EtOAc | HOAc | |
| 1 | Ru/n-Bu$_4$PBr/Co$_2$(CO)$_8$ (0.5:10:1) | 15 | $CO/H_2$ = 1:2 6500 psi 200° C. 17 hrs | 0 | 60 | 0 | 0 | 28 | 0 | ~100 |
| 2 | Ru/n-Bu$_4$PBr/Co$_2$(CO)$_8$ (0.5:10:1) | 15 | $CO/H_2$ = 1:1 6200 psi 200° C. 18 hrs | 0 | 58 | 0 | 0 | 32 | 0 | 66 |
| 3 | Ru/n-Bu$_4$PBr/Co$_2$(CO)$_8$ (1:10:0.5) | 10 | $CO/H_2$ = 1:2 6500 psi 200° C. 18 hrs | 0 | 56 | 0 | 8 | 4 | 0 | 14 |
| 4 | Ru/n-Bu$_4$PBr/Co$_2$(CO)$_8$ (0.5:10:1) | 15 | $CO/H_2$ = 1:1 6600 psi 250° C. 17 hrs | 0 | 20 | 12 | 16 | 3 | 6 | 190 |
| 5 | Ru/n-Bu$_4$PBr/Co$_2$(CO)$_8$/RuO$_2$ (0.5:10:1:0.5) | 20 | $CO/H_2$ = 1:1 6300 psi 200° C. 18 hrs | 0 | 5 | 44 | 0 | 16 | 7 | 50 |
| 6 | Ru/n-Bu$_4$PBr/Co$_2$(CO)$_8$/RuO$_2$ (0.5:10:0.5:1.0) | 20 | $CO/H_2$ = 1:1 6300 psi 200° C. 18 hrs | 33 | 5 | 19 | 17 | 7 | 0 | 110 |
| 7 | Ru/n-Bu$_4$PBr/Co$_2$(CO)$_8$/RuO$_2$ (0.5:10:1.0:0.1) | 15 | $CO/H_2$ = 1:1 6300 psi 200° C. 18 hrs | 13 | 11 | 26 | 5 | 7 | 0 | 50 |
| 8 | Ru/n-Bu$_4$PBr/Co$_2$(CO)$_8$/RuO$_2$ (0.5:10:1.0:0.05) | 15 | $CO/H_2$ = 1:1 8000 psi 200° C. 17 hrs | 0 | 43 | 10 | 13 | 2 | 0 | 130 |
| 9 | Ru/n-Bu$_4$PBr/Co$_2$(CO)$_8$/RuO$_2$ | 10 | $CO/H_2$ = 1:2 | 38 | 0 | 28 | 9 | 4 | 6 | 45 |

TABLE I-continued

Acetaldehyde Production from Co/H$_2$ Directly

| Example | Catalysts (mmole used) | p-dioxane Solvent, ml | Reaction Conditions | Product Selectivity, wt. % | | | | | | Productivity (g/mole Ru/hr) |
|---|---|---|---|---|---|---|---|---|---|---|
| | | | | MeOH | CH$_3$CHO | EtOH | MeOAc | EtOAc | HOAc | |
| | (2.0:10:0.5:1.0) | | 6150–4076 psi 200° C. 17 hrs | | | | | | | |
| 10 | Ru/n-Bu$_4$PBr/Co$_2$(CO)$_8$/RuO$_2$ (1.0:10:0.5:0.25) | 5 | CO/H$_2$ = 1:2 6300–4075 psi 200° C. 17 hrs | 0 | 0 | 14 | 3 | 40 | 4 | 15 |
| 11 | Ru/n-Bu$_4$PBr/Co$_2$(CO)$_8$/RhCl$_3$ (0.5:10:1.0:1.0) | 15 | CO/H$_2$ = 1:1 6300 psi 200° C. 17 hrs | 72 | 4 | 0 | 0 | 20 | 0 | 500 |

Many modifications may be made in the method of this invention by one skilled in the art without departing from the spirit and scope of this invention which are defined only in the appended claims. For example, the reactants, catalysts, promoters and solvents could have their proportions and modes of addition changed or the pressure and temperature could be altered to optimize the production of acetaldehyde.

We claim:

1. A process for preparing acetaldehyde which comprises contacting a mixture of carbon monoxide and hydrogen with an iodide-free catalyst system comprising elemental ruthenium, an iodide-free quaternary phosphonium or ammonium base or salt and a halide-free cobalt-containing compound at a pressure of 500 psig or greater, and at a temperature of about 150° C. or greater.

2. The process of claim 1 in which the reaction is conducted in the presence of a substantially inert, polar solvent.

3. The process of claim 1 in which the reaction is conducted in the presence of p-dioxane solvent.

4. The process of claim 1 in which the iodide-free quaternary phosphonium or ammonium base or salt is tetra-n-butylphosphonium bromide and the halide-free cobalt-containing compound is dicobalt octacarbonyl.

5. The process of claim 1 in which the elemental ruthenium is in the form of ruthenium powder.

6. A process for preparing acetaldehyde which comprises contacting a mixture of carbon monoxide and hydrogen with an iodide-free catalyst system comprising elemental ruthenium, an iodide-free quaternary phosphonium or ammonium base or salt and a halide-free cobalt-containing compound in the presence of ruthenium compounds and rhodium compounds as co-catalysts, at a pressure of 500 psig or greater, and at a temperature of about 150° C. or greater.

7. The process of claim 6 in which the reaction is conducted in the presence of a substantially inert p-dioxane solvent.

8. The process of claim 6 in which the iodide-free quaternary phosphonium or ammonium base or salt is tetra-n-butylphosphonium bromide and the halide-free cobalt-containing compound is dicobalt octacarbonyl.

9. The process of claim 6 in which the process is conducted at a pressure in the range of about 500 to about 10,000 psig.

10. The process of claim 6 in which the process is conducted at a pressure in the range of about 2,000 to about 10,000 psig.

11. The process of claim 6 in which the process is conducted at a temperature in the range of about 180° to 250° C.

12. A process for preparing acetaldehyde which comprises contacting a mixture of carbon monoxide and hydrogen with an iodide-free catalyst system comprising elemental ruthenium, tetra-n-butylphosphonium bromide and dicobalt octacarbonyl in the presence of p-dioxane solvent and a co-catalyst selected from the group consisting of rhodium(III) chloride and ruthenium(IV) oxide at a pressure of between about 2,000 and 10,000 psig and at a temperature between about 180° and 250° C.

* * * * *